US005496957A

United States Patent [19]
Glennon

[11] Patent Number: 5,496,957
[45] Date of Patent: Mar. 5, 1996

[54] TRYPTAMINE ANALOGS WITH 5-HT1D SELECTIVITY

[75] Inventor: Richard A. Glennon, Richmond, Va.

[73] Assignee: Virginia Commonwealth University, Richmond, Va.

[21] Appl. No.: 317,907

[22] Filed: Oct. 4, 1994

Related U.S. Application Data

[63] Continuation-in-part of Ser. No. 115,003, Sep. 1, 1993, abandoned.

[30] Foreign Application Priority Data

Aug. 31, 1994 [WO] WIPO ............... PCT/CA94/00476

[51] Int. Cl.$^6$ ........................................... C07D 209/04
[52] U.S. Cl. ........................................... 548/491
[58] Field of Search ................................. 548/491

[56] References Cited

U.S. PATENT DOCUMENTS

| | | | |
|---|---|---|---|
| 3,182,071 | 5/1965 | Shavel et al. | 260/319 |
| 3,317,560 | 5/1967 | Claassen | 260/326.15 |

FOREIGN PATENT DOCUMENTS

| | | | |
|---|---|---|---|
| 1137489 | 12/1982 | Canada. | |
| 0287468 | 10/1988 | European Pat. Off.. | |
| 0327426 | 8/1989 | European Pat. Off.. | |
| 6404604 | of 0000 | Netherlands. | |
| 191564 | of 0000 | U.S.S.R.. | |
| 859223 | 1/1961 | United Kingdom. | |
| 2186874 | 8/1987 | United Kingdom | 548/491 |
| WO91/06537 | 5/1991 | WIPO. | |
| 92/14708 | 9/1992 | WIPO | 548/491 |
| WO93/00333 | 1/1993 | WIPO. | |

OTHER PUBLICATIONS

Neth. Appl. 6,404,604, Chemical Abstract, vol. 64, No. 11180 (1965).
Soviet Union 191564, Abstract, 000530675 WPI Acc No.: 66-31247F/00 (1966).
Buznikov et al., "Sensitivity of Sea Urchin Early Embryos to Antagonists of Acetylcholine and Monoamines," *Experimental Cell Research*, vol. 86, pp. 317–324 (1974).
Buznikov et al., "The Sensitivity of Whole, Half and Quarter Sea Urchin Embryos to Cytotoxic Neuropharmacological Drugs," *Comp. Biochem. Physiol.*, vol. 64C, pp. 129–135 (1979).
Glennon "Central Serotonin Receptors as Targets for Drug Research," *Journal of Medicinal Chemistry*, vol. 30, No. 1, pp. 1–12 (1987).
Glennon et al., "Bufotenine Esters," *Journal of Medicinal Chemistry*, vol. 22, No. 11, pp. 1414–1416 (1979).
Glennon et al., "5-HT$_{1D}$ Receptors: A Serotonin Receptor Population for the 1990s," *DN&P*, vol. 6, No. 6, pp. 390–405 (Jul. 1993).
Glennon et al., "5-HT Receptor Ligands—Update 1992," *Current Drugs Ltd.*, pp. 1–45.
Glennon, "Serotonergic Agents and CNS Receptors," *Advances in CNS Drug-Receptor Interactions*, vol. 1, pp. 131–178 (1991).
Gomez–Jeria et al., "Quantum–Chemical Study of the Relation Between Electronic Structure and $_pA_2$ in a Series of 5-Substituted Tryptamines," *Int'l. Journal of Quantum Chemistry*, vol. XXVIII, pp. 421–428 (1985).
Gomez–Jeria et al., "Quantum Chemical Approach to the Relationship Between Molecular Structure and Serotonin Receptor Binding Affinity," *Journal of Pharmaceutical Sciences*, vol. 73, No. 12, pp. 1725–1728 (1984).
Gordeev et al., "Synthesis of 5-alkyltryptamines and 5-alkyl-alpha-methyltryptamines," *Mosk. Khim.–Tekhnol. Inst.*, No. 70, 110–15 (1972).
Hibert et al., "Serotonin (5-HT) Receptors," *Comprehensive Medicinal Chemistry*, vol. 3, ed. Sammes P., pp. 567–600, 1984.
Hiemke et al., "Gas–Liquid Chromatographic Properties of Catecholamines, Phenylethylamines and Indolalkylamines As Their Propionyl Derivatives," *Journal of Chromatography*, vol. 153, pp. 451–460 (1978).
Hino et al., "1-(1-Pyrrolin-2-yl)-β-carbolines. Synthesis of Eudistomins H, I, and P$^1$)," *Chem. Pharm. Bull.*, vol. 37, No. 10, pp. 2596–2600 (1989).
Landau et al., "Sensitivity of Sea Urchin Embryos to Cytotoxic Neuropharmacological Drugs, The Correlations Between Activity and Lipophility of Indole and Benzole Derivatives," *Comp. Biochem. Physiol.*, vol. 69C, pp. 359–366 (1981).

(List continued on next page.)

Primary Examiner—Joseph K. McKane
Attorney, Agent, or Firm—Foley & Lardner

[57] ABSTRACT

Described herein are tryptamine analogs that display high binding affinity and selectivity for the 5-HT1Dβ receptor, of the formula:

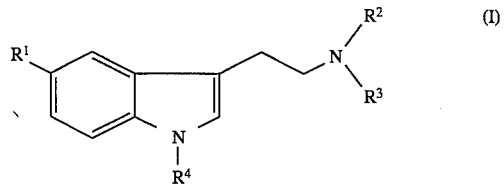

wherein
  R$^1$ represents a chain selected from C$_{8-11}$alkyl, C$_{7-10}$alkoxy, C$_{8-11}$alkanoyl and C$_{7-10}$alkanoyloxy wherein said chain is optionally substituted by hydroxyl, C$_{1-4}$alkyl or C$_{1-4}$alkoxy and wherein one of the intervening carbons of said chain is optionally replaced with a heteroatom selected from oxygen, nitrogen and sulfur;
  R$^2$ and R$^3$ each independently represent H or C$_{1-3}$alkyl; and
  R$^4$ represents H, C$_{1-4}$alkyl, aryl or arylC$_{1-4}$alkyl;

The compounds are useful as reagents for receptor identification and in receptor-based drug screening programs, and can also be used therapeutically to treat conditions for which administration of a 5-HT1D ligand is indicated, for example in the treatment of migraine.

22 Claims, No Drawings

OTHER PUBLICATIONS

Morozovskaya et al., "O–acyl Derivatives of Serotonin," *Pharm. Chem. Journal,* vol. 3, pp. 125–128 (1968).

Sleight et al., "Identification of 5-hydroxytryptamine$_{1A}$ Receptor Agents Using a Composite Pharmacophore Analysis and Chemical Database Screening," *Arch Pharmacology,* vol. 343, pp. 109–116 (1991).

Strandtmann et al., "Acyltryptamines. II. Synthesis of Acyltryptamines, Indazoles, and Azepinoindoles from the Acylphenylhydrazones of 2,3-Piperidinedione[1]," *J. Med. Chem.,* vol. 6, pp. 719–721 (Nov. 1963).

Suvorov et al., (Abstract) *Zh. Obshch. Khim.,* vol. 46(5), 1165–75 (1976).

Vasin et al., (Abstract) *Radiobiologiya,* vol. 24, No. 3, pp. 411–414 (1984).

Suvorov, et al., Chemical Abstract No. 70637p, Heterocycles, vol. 80, No. 13, Apr. 1, 1974.

Street, et al., "Synthesis and Serotonergic Activity of 5–(Oxadiazolyl)tryptamines: Potent Agonists for 5–HT$_{1D}$ Receptors", *J. Med. Chem.,* vol. 36:1529–1538 (1993).

CA 64:11180g, Indolylalkylguanidines, Gloeilampenfabrieken, (1966).

Gordeev, et al., "Synthesis of 5–alkyltryptamines and 5–alkyl–α–methyl tryptamines", p. 485, (1973).

Suvorov, et al., "Indole Derivatives. XXII Improved Tryptamine Synthesis", *Zh Obshch Khim,* vol. 34:1595, (1964).

Suvorov, et al., "Amino Acid And Peptide Derivatives Of Biogenetic Amines. IX. Synthesis of O,N–amino Acid Derivatives Of Serotonin And Their Mass Spectrometric And Pharmacological Study", *Zh Obshch Khim,* vol. 46(5):1165 (1976).

Vasin, et al., "Role Of The Serotonin Hydroxyl Group In Pharmacological And Radioprotectant Action Of Serotonin" *Radiobiologiya,* vol. 24(3):411, (1984).

CA 101:146879u Role of . . . Serotonin. Vasin et al., p. 319, 1984.

CA 114:221894u A new . . . sites. Boulenguez et al., pp. 147–148, 1991.

TRYPTAMINE ANALOGS WITH 5-HT1D SELECTIVITY

This application is a CIP of application Ser. No. 08/115,003, filed Sep. 1, 1993, now abandoned.

This invention relates to tryptamine analogs having 5-HT receptor binding activity, and to their production and use.

BACKGROUND TO THE INVENTION

Through its interaction with receptors borne on neuronal and other cells, 5-hydroxytryptamine (5-HT; serotonin), exerts various physiological effects. Imbalances in this interaction are believed responsible for such conditions as anxiety, depression, hallucination, migraine, chemotherapy-induced nausea, and for disorders in sexual activity, cardiovascular activity and thermoregulation, among others. From an improved understanding of the 5-HT receptor population, it is apparent that these effects are mediated selectively through individual types and sub-types of 5-HT receptors.

Migraine, for example, has been treated with ergotamine, dihydroergotamine and methysergide, all of which act at 5-HT1 type receptors. Their use is associated with undesirable side effects, however, likely because they interact also with various other 5-HT receptor types. An improved side effect profile is seen with the more recently marketed tryptamine analog known as sumatriptan, which binds somewhat selectively at the 5-HT1 receptor sub-type known as 5-HT1D (see Glennon and Westkaemper, DN&P, 1993, 6 (6):390).

Given the physiological and clinical significance of the 5-HT1D receptor, it would be desirable to provide compounds capable of binding tightly and selectively to this receptor, for medical use for example to treat indications such as migraine and others for which administration of a 5-HT1D ligand is indicated, and also for research and diagnostic use for example to identify these receptors and to screen for drug candidates.

SUMMARY OF THE INVENTION

The present invention provides tryptamine analogs of formula (I) and salts, solvates or hydrates thereof:

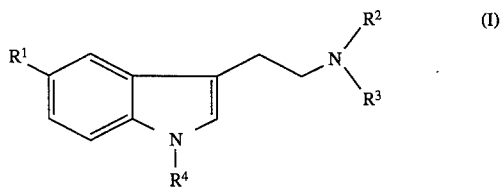

wherein $R^1$ represents a chain selected from $C_{8-11}$alkyl, $C_{7-10}$alkoxy, $C_{8-11}$alkanoyl and $C_{7-10}$alkanoyloxy wherein said chain is optionally substituted by hydroxyl, $C_{1-4}$alkyl or $C_{1-4}$alkoxy and wherein one of the intervening carbons of said chain is optionally replaced with a heteroatom selected from oxygen, nitrogen and sulfur;

$R^2$ and $R^3$ each independently represent H or $C_{1-3}$alkyl; and $R^4$ represents H, $C_{1-4}$alkyl, aryl or aryl$C_{1-4}$alkyl;

In another of its aspects, the present invention provides processes for preparing compounds of formula (I) and intermediates useful in such processes.

In a further aspect, the present invention provides compositions containing the present compounds either for use as reagents for example in the identification of 5-HT1D receptors or in screening for ligands of such receptor, or for use pharmaceutically to treat conditions where a 5-HT1D ligand is indicated.

The invention is now described in greater detail with reference to the accompanying FIG. 1, which illustrates the stimulatory effect of a compound of the invention on cells presenting the 5-HT1D receptor.

DETAILED DESCRIPTION OF THE INVENTION AND PREFERRED EMBODIMENTS

The present invention provides tryptamine analogs that bind with relative high affinity and selectivity to the 5-HT1D receptor. Compounds having this desirable combination of properties are tryptamine analogs in which the 5-position is substituted by a group, designated $R^1$, having a length in the range from 8 to 11 atoms.

In particular and with reference to Formula I, the group $R^1$ can be selected from linear $C_{8-11}$alkyl, $C_{8-11}$alkanoyl, $C_{7-10}$alkoxy in which the ether oxygen is attached at the 5-position, and $C_{7-10}$alkanoyloxy in which the ester oxygen is attached at the 5-position. These groups suitably have a chain length of 8–11, and most suitably of 8, 9 or 10 atoms.

In specific embodiments of the invention, $R^1$ is $C_{7-10}$alkoxy, preferably $C_{7-9}$alkoxy and most preferably $C_9$alkoxy (nonyloxy).

The alkyl, alkoxy, alkanoyl or alkanoyloxy chain constituting $R^1$ can be substituted by one or more e.g. up to 4 substituents, suitably 1 or 2 substituents, selected from hydroxyl; linear or branched chain $C_{1-4}$alkyl such as methyl, ethyl, propyl (n- and i-), butyl (n-, i- and t-); and linear or branched chain $C_{1-4}$alkoxy such as methoxy, ethoxy, propoxy (n- and i-) and butoxy (n-, i- and t-). In specific embodiments, $R^1$ is the group 8-hydroxyoctyloxy or the group 7,7-dimethyloctyloxy.

A substituent may be conjugated to any one of the carbons within the carbon chain of the group constituting $R^1$. In selecting $R^1$ substituents, it is desirable to maintain the total chain length of $R^1$ to within the 8 to 11 atom range, ie. $C_{7-10}$ alkoxy and alkanoyloxy and $C_{8-11}$ alkyl and alkanoyl. Thus, were $R^1$ to represent an alkoxy-substituted alkyl group, the alkyl group and alkoxy group are desirably selected to provide a total chain length not in excess of 11, and most preferably in the 7–10 range. In embodiments of the invention, the alkyl, alkoxy, alkanoyl or alkanoyloxy chain of $R^1$ is substituted by an $C_{1-4}$alkyl, or hydroxyl group. In specific embodiments of the invention, the $R^1$ chain is substituted with one or two methyl groups or a hydroxyl group.

The alkyl, alkoxy, alkanoyl or alkanoyloxy chain constituting $R^1$ can be interrupted by replacement of one or more carbon atoms within the chain with a heteroatom such as nitrogen, oxygen or sulfur. The total chain length of is maintained in the 8–11 atom range. In embodiments of the invention, the alkyl, alkoxy, alkanoyl or alkanoyloxy chain of $R^1$ is interrupted by the replacement of a carbon atom with an oxygen atom. In specific embodiments, $R^1$ represents the group 6-ethyloxy-hexyloxy or 4-butyloxy-butyloxy.

$R^2$ and $R^3$ are selected independently from H, and $C_{1-3}$alkyl such as methyl and ethyl. In embodiments of the invention, at least one of $R^2$ and $R^3$ is H. In preferred embodiments of the invention, both $R^2$ and $R^3$ are H.

$R^4$ is selected independently from H, $C_{1-4}$alkyl, aryl such as phenyl and aryl$C_{1-4}$alkyl such as benzyl and phenethyl. In specific embodiments of the invention, $R^4$ is H.

Particular compounds of formula (I) include:

3-(2-aminoethyl)-5-heptyloxyindole 3-(2-aminoethyl)-5-octyloxyindole 3-(2-aminoethyl)-5-nonyloxyindole 3-(2-aminoethyl)-5-decyloxyindole 3-(2-aminoethyl)-5-(7,7-dimethyloctyloxy) indole 3-(2-aminoethyl)-5-(4-butyloxybutyloxy) indole 3-(2-aminoethyl)-5-(6-ethyloxyhexyloxy) indole 3-(2-aminoethyl)-5-(8-hydroxyoctyloxy)indole and (N-methyl-2-aminoethyl)—and (N,N-dimethyl-2-aminoethyl)-analogs thereof;

3-(2-aminoethyl)-5-octanoylindole 3-(2-aminoethyl)-5-nonanoylindole 3-(2-aminoethyl)-5-decanoylindole 3-(2-aminoethyl)-5-undecanoylindole and (N-methyl-2-aminoethyl)—and (N,N-dimethyl-2-aminoethyl)-analogs thereof; and 3-(2-aminoethyl)-5-heptanoyloxyindole 3-(2-aminoethyl)-5-octanoyloxyindole 3-(2-aminoethyl)-5-nonanoyloxyindole 3-(2-aminoethyl)-5-decanoyloxyindole and (N-methyl-2-aminoethyl)—and (N,N-dimethyl-2-aminoethyl)-analogs thereof.

Acid addition salts of the compounds of formula (I) include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates, may be used for example in the isolation of compounds of formula (I) for reagent use, or for subsequent conversion to a pharmaceutically acceptable acid addition salt. Also included within the scope of the invention are solyates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of formula (I) for example where $R^1$ is substituted $C_{8-11}$alkyl, $C_{7-10}$alkoxy, $C_{8-11}$alkanoyl or $C_{7-10}$alkanoyloxy, may contain an asymmetric center. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of formula (I) or a salt, solvate or hydrate thereof, which comprises:

(a) in the case where $R^1$ is $C_{7-10}$alkoxy and $R^2$ and $R^3$ are H, deprotecting by treatment with a suitable cleaving agent an intermediate of the structure (II):

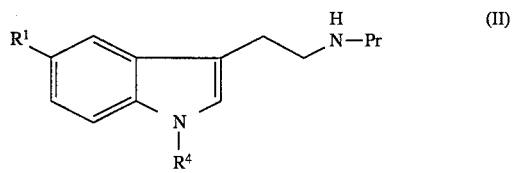

wherein $R^4$ are as defined above and Pr represents a protecting group. In a preferred embodiment, Pr represents acetyl or trifluoroacetyl, and the cleaving agent is an inorganic acid such as HCl or a base such as KOH.

The protected structure (II) itself can be prepared by the steps of:

(i) obtaining an intermediate of structure (III):

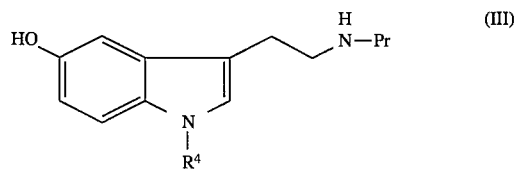

wherein $R^4$ and Pr are as just defined; and then, (ii) reacting the intermediate of structure (III) with the corresponding alkylhalide.

Structure (III) can be obtained by debenzylating the corresponding 5-benzyloxy structure, itself obtained by amidating the 5-benzyloxy structure to incorporate the protecting group, Pr.

To generate products in which both $R^2$ and $R^3$ are alkyl groups, synthesis can proceed by (i) obtaining an intermediate of structure (IV)

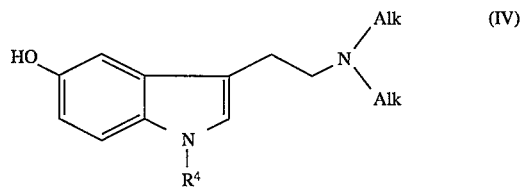

and then (ii) reacting the intermediate of structure (IV) with the appropriate alkylhalide in the case where $R^1$ is an alkoxy group or with the appropriate alkanoylhalide in the case where $R^1$ is an alkanoyloxy group.

As an alternative to the synthetic routes just described, and particularly for the production of compounds in which one or both of $R^2$ and $R^3$ are $C_{1-4}$alkyl, compounds of Formula I can be prepared by the steps of obtaining an intermediate of structure (V)

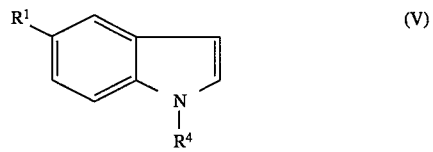

wherein $R^1$ is an alkyl or alkoxy and $R^4$ is defined above, and then elaborating to the corresponding aminoethyl or substituted amino ethyl. This elaboration can be achieved using standard procedures common to the art, for instance, by reaction of intermediate (V) with oxalyl chloride and subsequent amidation by reaction with $NHR^2R^3$. Reduction of the resulting glyoxylic amide with a suitable reducing agent, such as lithium aluminum hydride, will provide the desired compound of Formula (I).

To generate compounds wherein one or both of $R^2$ and $R^3$ are $C_{1-4}$alkyl, and $R^1$ is an alkanoyl or alkanoyloxy, the intermediate (VI) is prepared from 5-hydroxy indole which is O-protected and reacted with oxalyl chloride and subsequently amidated by reacting with NHR²R³. Reduction of the resulting glyoxylic amide with a suitable reducing agent, such as lithium aluminum hydride, provides the intermediate compound (VI)

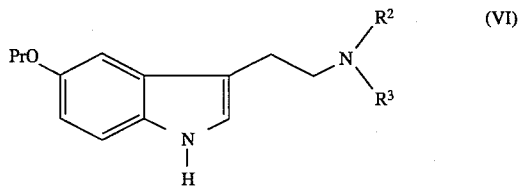

Intermediate (VI) is used to generate N-substituted 3-aminoethyl compounds wherein R¹ is an alkanoyloxy by deprotecting the 5-hydroxy and subsequently reacting with an acylchloride. Alternatively, (VI) is used to generate the corresponding alkanoyl by reacting with trifluoroacetic anhydride followed by a catalyst, Pd(OAc)₂, carbon monoxide and methanol to yield a 5-methoxycarbonyl intermediate which is converted to the corresponding 5-carboxy compound upon hydrolysis with LiOH in water and methanol. The carboxy intermediate is converted to a Weinreb amide by reacting with N-methyl-methoxyamine and a coupling agent EDCI and a catalyst DMAP (dimethylaminopyridine). The Weinreb amide is then reacted with a Grignard reagent to yield the desired N-substituted 3-aminoethyl-5-alkanoyl compound of the invention. The following scheme represents the synthesis of 5-alkanoyl compounds having one or both of R² and R³ substituted with C₁₋₄alkyl.

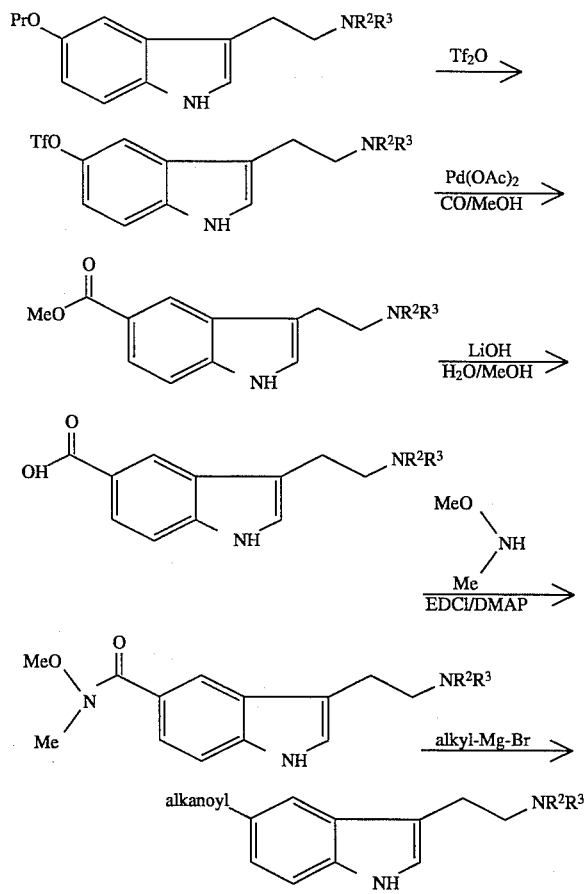

To generate products in which R⁴ is other than H, synthesis can proceed by (i) obtaining a compound of structure (VII)

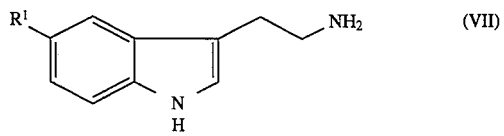

by methods herein described where R¹ is alkoxy, alkyl, alkanoyl or alkanoyloxy; ii) protecting the aminoethyl nitrogen with a suitable protecting group, for example phthalimide to give a compound of structure (VIII)

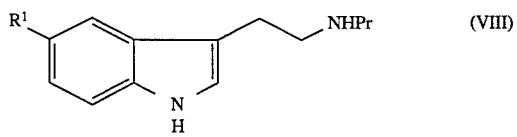

iii) reacting compound (VIII) with the desired alkyl, aryl or arylalkyl halide and then iv) deprotecting the aminoethyl group with an appropriate deprotecting agent, eg. with hydrazine when the protecting group is a phthalimide.

In the case where R¹ is C₈₋₁₁alkyl and R², R³ and R⁴ are hydrogen the following general procedure may be used. The synthetic scheme originates from the position 5 substituent and proceeds to the formation of the indole ring by cyclization followed by activation at the 3 position and subsequent addition of the aminoethyl group. Synthesis begins by obtaining, from commercial sources or by synthesis, aniline substituted at the para position with the desired C₈₋₁₁alkyl group. It will be appreciated that various substitutions may be introduced on the alkyl group by incorporation of the substituent at this step of the synthesis provided the substituent is stable under subsequent reaction conditions or is protected with an appropriate protecting group. Suitable substituents include hydroxyl, and linear or branched alkyl or alkoxy chains of 4 or fewer carbon atoms such that the total chain length is 8–11 atoms. Further, the C₈₋₁₁alkyl chain may have one or more carbons replaced with a heteroatom such as nitrogen oxygen or sulfur provided that the heteroatom is stable under the reaction conditions or is appropriately protected.

5-alkyl-substituted 2-alkoxycarbonylindole is obtained by reacting the para-substituted aniline with first sodium nitrite and HCl and then 2-methylaceto-acetate and KOH. The 2-alkoxy carbonyl group is removed with a suitable reagent such as KOH and the 3-position is activated with POCl₃ and dimethylformamide (DMF) to give a 5-substituted 3-formyl indole compound. This is converted to a 5-substituted 3-(2-nitro)-ethenyl indole compound by reacting with nitromethane and ammonium acetate. Finally, reaction with lithium aluminum hydride (LiAlH₄) in tetrahydrofuran (THF) yields the desired 3-(2-aminoethyl)-5-alkylindole compound of the invention. The following is a schematic representation of the synthesis of 5-alkyl compounds of the invention:

In the case where R¹ is C₈₋₁₁alkanoyl and R², R³ and R⁴ are hydrogen, the following general procedure described in

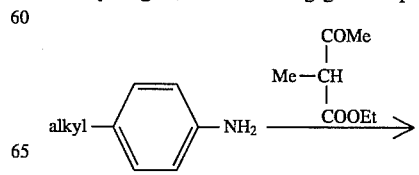

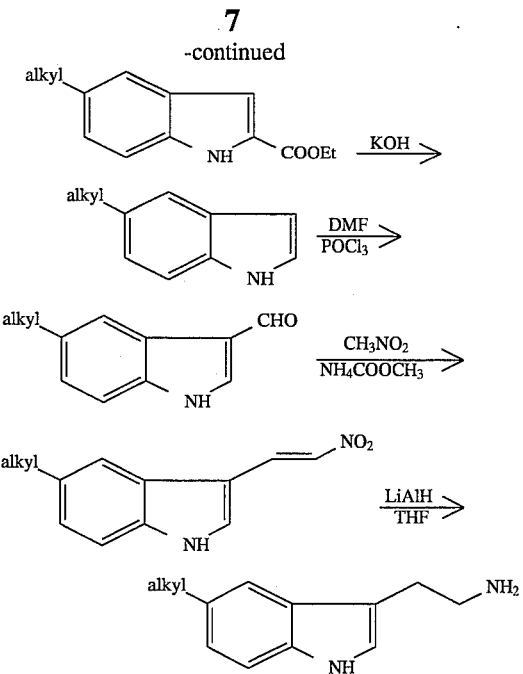

Strandtmann et al, J. Med. Chem. (1963) 6:719 may be used. Commercially obtained or synthesized $C_{8-11}$ alkanoyl-substituted benzenediazonium salt is coupled with 3-carboxy-2-piperidone to give a hydrazone. Cyclization of the hydrazone forms a 6-alkanoyl-1,2,3,4-tetrahydro-1-oxo-β-carboline which is converted to the corresponding 3-(2-aminoethyl)-5-alkanoyl-2-carboxy-tryptamine by base-catalyzed hydrolysis. Decarboxylation by refluxing with HCl yields the desired 3-(2-amino-ethyl)-5-alkanoylindole. It will be appreciated that the alkanoyl- benzenediazonium salt may have substituents on the alkanoyl chain such as $C_{1-4}$alkyl or $C_{1-4}$alkoxy. Suitable substituents are those that are stable under coupling, cyclization, hydrolysis and decarboxylation reaction conditions. Further, the alkanoyl chain may have one or more carbons replaced with a heteroatom such as nitrogen oxygen or sulfur provided that the heteroatom is stable under the reaction conditions or is protected by a suitable protecting group common in the art. The following is a schematic representation of the synthesis of 5-alkanoyl compounds of the invention:

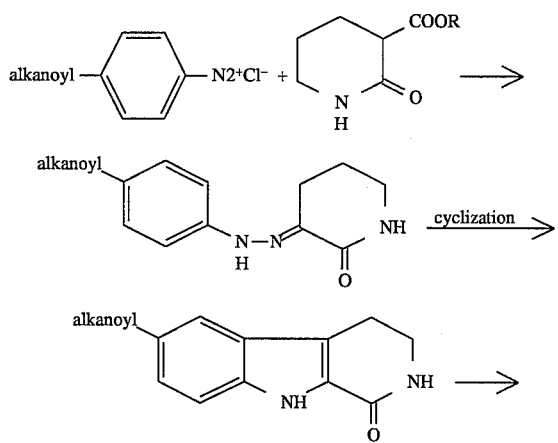

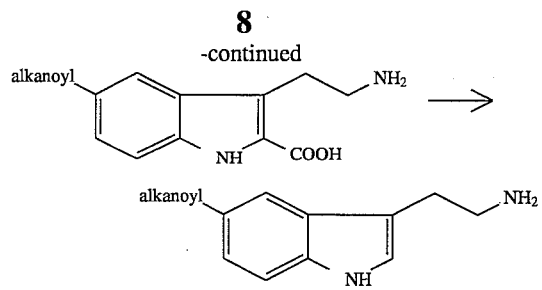

For use as a reagent, the present compounds can be stored in packaged form for reconstitution and use. The compounds, and particularly the preferred nonyloxy compound, can be used to identify 5-HT1D receptors within a population of 5-HT receptors. This can be achieved by incubating the receptors in the presence or absence of the selected compound and then incubating the resulting preparation with a radiolabeled 5-HT ligand, such as $^3$H-5-HT or $^3$H-8-OH-DPAT. The 5-HT1D receptors are thus revealed as those receptors that are not labeled when pre-incubated with a selected compound of the present invention. In a preferred embodiment of the invention, this procedure is exploited for the purpose of identifying 5-HT1Dβ receptors and, as ligand, the compound 3-(2-aminoethyl)-5-nonyloxy-indole.

In another embodiment of the invention, the compound is provided in labelled form, such as radiolabeled form e.g. labelled by incorporation within its structure of $^3$H or $^{14}$C or by conjugation to $^{125}$I. Such radiolabeled forms can be used to directly to distinguish between 5-HT1A and 5-HT1D receptors. Furthermore, radiolabeled forms of the present compounds can be exploited to screen for more potent 5-HT1D ligands, by determining the ability of the test ligand to displace the radiolabeled compound of the present invention.

The sumatriptan-like binding profile of the present compounds indicates their utility as pharmaceuticals that may be useful for the treatment of various conditions in which the use of a 5-HT1Dβ ligand is indicated, such as for the treatment of migraine, cluster headache and portal tension, a condition characterized by,increased portal vein blood flow and typically associated with cirrhosis of the liver.

For use in medicine, the compounds of the present invention are usually administered in a standard pharmaceutical composition. The present invention therefore provides in a further aspect pharmaceutical compositions comprising a compound of structure (I) or a pharmaceutically acceptable salt, solvate or hydrate thereof and a pharmaceutically acceptable carrier.

The compounds of the present invention may be administered by an convenient route, for example by oral, parenteral, buccal, sublingual, nasal, rectal or transdermal administration and the pharmaceutical compositions adapted accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule.

Each dosage unit for oral administration may suitably incorporate from 1 to 250 mg (and for parenteral administration contains preferably from 01. to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous, or intramuscular dose of between 0.1 mg and 100 mg, preferably between 0.1 mg and 50 mg, e.g., between 1 mg and 25 mg, of the compound of formula (I) or a pharmaceutically acceptable salt, solvate or hydrate thereof calculated as the free base, the compound being administered 1 to 4 times per day. Suitably, the compounds will be administered for a period of continuous therapy, for example for a week or more.

EXAMPLE 1

3-(2-Acetamidoethyl)-5-hydroxyindole

The captioned compound served as an intermediate in the preparation of the compounds hereinafter exemplified. To produce this intermediate, a suspension of 5-benzyl-oxytryptamine (1.9 g, 7.13 mmol) as free base in 10% HCl (30 mL) was treated with NaOAc (20 g) and the solution volume was adjusted to about 80 mL with water. The mixture was allowed to stir at room temperature for 30 min; a few pieces of ice chips were added followed by acetic anhydride (20 mL) and the reaction mixture was allowed to stir for 1 h. The precipitated materials were collected, washed with water (2×20 mL), and the solid was recrystallized from $CH_2Cl_2$/MeOH to give 1.62 g (74%) of the 5-benzyloxy analog of the title compound as a white solid, mp 133–°134° C.

A solution of the benzyloxy analog (2.2 g, 7.13 mmol) in absolute EtOH (50 mL) was next treated with Raney Nickel (4.4 g) in a Parr hydrogenation bottle and hydrogenated at 40 p.s.i. overnight. The catalyst was removed by filtration through a Celite pad and the filtrate was concentrated under reduced pressure to give an oil. The oil was purified by column chromatography using a solvent system of $CH_2Cl_2$/MeOH (90:10) to give 1.48 g (95.1%) of the title intermediate as an oil.

EXAMPLE 2

3-(2-aminoethyl)-5-heptyloxyindole hemioxalate

A suspension of 5-benzyloxytryptamine (1.9 g, 7.13 mmol) as free base in 10% HCl (30 mL) was treated with NaOAc (20 g) and the solution volume was adjusted to about 80 mL with water. The mixture was allowed to stir at room temperature for 30 min; a few pieces of ice chips were added followed by acetic anhydride (20 mL) and the reaction mixture was allowed to stir for 1 h. The precipitated materials were collected, washed with water (2×20 mL) and the solid was recrystallized from $CH_2Cl_2$/hexane to give the acetylated derivative as a white solid.

A solution of this N-acetyl compound (2.2 g, 7.13 mmol) in absolute EtOH (50 mL) was treated with Raney Nickel (4.4 g) in a Parr hydrogenation bottle and hydrogenated at 40 p.s.i. overnight. The catalyst was removed by filtration through a Celite pad and the filtrate was concentrated under reduced pressure to give an oil. The oil was purified by column chromatography using a solvent system of $CH_2Cl_2$/MeOH (90:10) to give the phenol as an oil.

A stirred mixture of the phenol (0.45 g, 2.07 mmol), 1-bromoheptane (1.75 g, 11.59 mmol), anhydrous $K_2CO_3$ (0.94 g, 6.83 mmol), and MeOH (7 mL) in 2-butanone (40 mL) was heated at reflux overnight under $N_2$. After allowing to cool to room temperature, the reaction mixture was filtered and the liltrate was concentrated under reduced pressure to give an oil. A solution of the oil in $CH_2Cl_2$ (50 mL) was washed successively with 2N NaOH (1×30 mL) and water (1×30 mL). The organic portion was dried ($MgSO_4$) and solvent was removed under reduced pressure to give an oil. The oil was purified by column chromatography using a solvent system of $CH_2Cl_2$/MeOH (90:10) to give the O-alkylated product as an oil. Without further purification, the resulting oil in 2N HCl (10 mL) was heated at reflux for 20 h. After allowing the reaction mixture to cool to room temperature, 2N NaOH (20 mL) was added and the reaction mixture was extracted with $CH_2Cl_2$ (2×30 mL). The combined organic portions were washed with water (1×30 mL), dried ($MgSO_4$), and the solvent was removed under reduced pressure to give an oil. The resulting oil was purified by column chromatography using a solvent system of $CH_2Cl_2$/MeOH (90:10). The combined fractions from the column were evaporated under reduced pressure to give 3-(2-aminoethyl)-5-heptyloxyindole as an oil. The oil in anhydrous $Et_2O$ (5 mL) was added to a saturated ethereal solution of oxalic acid. The resultant salt was collected by filtration, washed with anhydrous Et$_2$O (2×10 mL), and recrystallized from MeOH/Et$_2$O to give a white solid, mp 192°–194° C. Anal. (C$_{34}$H$_{42}$N$_4$O$_2$·C$_2$H$_2$O$_4$·0.25H$_2$O): C,H, N.

EXAMPLE 3

3-(2-aminoethyl)-5-octyloxyindole oxalate

In the manner described in example 2, but using 1-bromooctane in place of 1-bromoheptane, there was produced 3-(2-aminoethyl)-5-octyloxyindole oxalate (white solid, mp 136°–139° C. Anal. (C$_{18}$H$_{28}$N$_2$O)). Similarly, 3-(2-aminoethyl)-5-decyloxyindole was produced from 1-bromodecane.

EXAMPLE 4

3-(2-aminoethyl)-5-nonyloxyindole oxalate

The intermediate produced as described in Example 1 (0.45 g, 2.07 mmol) was mixed under stirring with 1-bromononane (1.75 g, 11.59 mmol), anhydrous K$_2$CO$_3$ (0.94 g, 6.83 mmol), and MeOH (7 mL) in 2-butanone (40 mL) and was heated at reflux overnight under N$_2$. After allowing to cool to room temperature, the reaction mixture was filtered and the filtrate was concentrated under reduced pressure to give an oil. A solution of the oil in CH$_2$Cl$_2$ (50 mL) was washed successively with 2N NaOH (1×30 mL) and water (1×30 mL). The organic portion was dried (MgSO$_4$) and solvent was removed under reduced pressure to give an oil. The oil was purified by column chromatography using a solvent system of CH$_2$Cl$_2$/MeOH (90:10) to give 0.53 g of the O-alkylated product as an oil. Without further purification, the resulting oil in 2N HCl (10 mL) was heated at reflux for 20 h. After allowing the reaction mixture to cool to room temperature, 2N NaOH (20 mL) was added and the reaction mixture was extracted with CH$_2$Cl$_2$ (2×30 mL). The combined organic portions were washed with water (1×30 mL), dried (MgSO$_4$), and the solvent was removed under reduced pressure to give an oil. The resulting oil was purified by column chromatography using a solvent system of CH$_2$Cl$_2$/MeOH (90:10). The combined fractions from the column were evaporated under reduced pressure to give 0.16 g (31%) of the free base of the title compound as an oil. The oil in anhydrous Et$_2$O (5 mL) and added to a saturated ethereal solution of oxalic acid. The resultant oxalate salt was collected by filtration, washed with anhydrous Et$_2$O (2×10 mL), and recrystallized from MeOH/Et$_2$O to give the title salt compound as a white solid, mp 148°–150° C. Anal. (C$_{21}$H$_{32}$N$_2$O$_5$): C,H,N.

EXAMPLE 5

3-(2-aminoethyl)-5-(8-hydroxyoctyloxy)-indole hydrochloride

To a stirred mixture of serotonin creatinine sulfate monohydrate (1 g, 2.58 mmol), K$_2$CO$_3$ (0.712 g, 5.16 mmol) in H$_2$O (15 mL) was added di-tert-butyl-dicarbonate (0.56 g, 2.58 mmol). The resulting mixture was stirred for 24 h at room temperature. The reaction mixture was extracted into EtOAc (3×16 mL) and washed with H$_2$O (11 mL), 5% HCl (11 mL) and brine solution (20 mL). The organic portion was dried (MgSO$_4$) and evaporated to dryness to give 0.69 g (96%) of N-t-BOC-serotonin as yellow/brown foam: mp 52°–54° C.

A mixture of N-t-BOC-serotonin (0.69 g, 2.50 mmol), 1-bromo-8-tetrahydropyranyloxyoctane (0.73 g, 2.50 mmol) and K$_2$CO$_3$ (0.66 g, 4.56 mmol) in acetonitrile (9 mL) was heated to reflux for 24 h under N$_2$ with stirring. After cooling to room temperature the solid was removed by filtration and solvent evaporated under reduced pressure to give an oil. The oil was purified by flash column chromatography using EtOAc/Hexane (1:3) as the eluent. The product (0.82 g, 67%) was collected as a yellow oil and triturated with hexane to give 3-(N-t-BOC-2-amino-ethyl)-5-(8-tetrahydrophyranyloxyoctyloxy) indole, yellow solid, mp 56°–58° C.

A mixture of 3-(N-t-BOC-2-aminoethyl)-5-(8-tetra-hydropyranyloxyoctyl) indole (100 mg, 0.2 mmol) and pyridinium p-toluenesulfonate (5.1 mg, 0.02 mmol) in 2 mL EtOH was heated at 55° C. for 5 h. The solvent was removed under reduced pressure and purified by column chromatography using a solvent system of EtOAc/Hexane (1:3) to afford 70 mg (85%) of 3-(N-t-BOC-2-aminoethyl)-5-(8-hydroxyoctyloxy) indole as an oil.

To a mixture of 3-(N-t-BOC-2-aminoethyl)-5-(8-hydroxyoctyloxy) indole (70 mg, 0.17 mmol) in dry Et$_2$O (2 mL) was added an ethereal of 3M HCl (10 mL). The mixture was stirred for 5 h. The precipitated product was filtered and washed with Et$_2$O. The salt was recrystallized from absolute EtOH/Et$_2$O to afford 30mg (51%) of HL-110, mp 180°–182° C. Anal. (C$_{18}$H$_{28}$N$_2$O$_2$·HCl): C, H, N.

EXAMPLE 6

3-(2-aminoethyl)-5-(7-methyloctyloxy)-indole hydrochloride

A mixture of N-t-BOC-serotonin (276 mg, 1 mmol), 1-bromo-7-methyloctane (310 mg, 1.5 mmol) and K$_2$CO$_3$ (207 mg, 1.5 mmol) in acetonitrile (20 mL) was refluxed for 24 h under N$_2$ with stirring. After cooling to room temperature the solid was removed by filtration and solvent evaporated under reduced pressure to give an oil. The oil was purified by column chromatography (25% EtOCAc/hexane) to give 2.93 mg (73%) of 3-(N-t-BOC-2-aminoethyl)-5-(7-methyloctyloxy) indole as an oil.

To a solution of 3-(N-t-BOC-2-aminoethyl)-5-(7-methyloctyloxy) indole (403 mg, 1 mmol) in EtOAc (5 mL) was added 3N HCl in EtOAc (15 mL). The mixture was stirred for 2 h. The precipitated product was filtered and washed with EtOAc and Et$_2$O to give 332 mg (70%) of 3-(2-aminoethyl)-5-(7-methyloctyloxy) indole hydrochloride. Analytical sample was recrystallized from MeOH/Et$_2$O: mp 193°–195° C. (dec). Anal. calcd. for (C$_{19}$H$_{30}$N$_2$O·HCl): C,H,N.

EXAMPLE 7

3-(2-aminoethyl)-5-(7,7-dimethyloctyloxy)-indole hydrochloride

A mixture of N-t-BOC-serotonin (276 mg, 1 mmol), 1-bromo-7,7-dimethyloctane (310 mg, 1.5 mmol) and K$_2$CO$_3$ (207 mg, 1.5 mmol) in acetonitrile (20 mL) was refluxed for 24 h under N$_2$ with stirring. After cooling to room temperature the solid was removed by filtration and solvent evaporated under reduced pressure to give an oil. The oil was purified by column chromatography (25% EtOCAc/hexane) to give 3-(N-t-BOC-2-aminoethyl)-5-(7,7-dimethyloctyloxy)indole as an oil.

To a solution of 3-(N-t-BOC-2-aminoethyl)-5-(7,7-dimethyloxyloxy) indole (403 mg, 1 mmol) in EtOAc (5 mL) was added 3N HCl in EtOAc (15 mL). The mixture was stirred for 2 h. The precipitated product was filtered and washed with EtOAc and Et$_2$O to give (62%) 3-(2-aminoethyl)-5-(7,7-dimethyloctyloxy) indole hydrochloride. Analytical sample was recrystallized from MeOH/Et$_2$O: mp 173°–175° C. Anal. calcd. for (C$_{20}$H$_{33}$N$_2$OCl·0.5H$_2$O).

EXAMPLE 8

3-(2-aminoethyl)-5-(6-ethyloxyhexyloxy)-indole hydrochloride

A mixture of N-t-BOC-serotonin (276 mg, 1 mmol), 1-bromo-6-ethyloxyhexane (310 mg, 1.5 mmol) and K$_2$CO$_3$ (207 mg, 1.5 mmol) in acetonitrile (20 mL) was refluxed for 24 h under N$_2$ with stirring. After cooling to room temperature the solid was removed by filtration and solvent evaporated under reduced pressure to give an oil. The oil was purified by column chromatography (25% EtOCAc/hexane) to give 3-(N-t-BOC-2-aminoethyl)-5-(6-ethyloxyhexyloxy) indole as an oil.

To a solution of 3-(N-t-BOC-2-aminoethyl)-5-(6-ethyloxy-hexyloxy) indole (403 mg, 1 mmol) in EtOAc (5 mL) was added 3N HCl in EtOAc (15 mL). The mixture was stirred for 2 h. The precipitated product was filtered and washed with EtOAc and Et$_2$O to give (74%) 3-(2-aminoethyl)-5-(6-ethyloxyhexyloxy) indole hydrochloride. Analytical sample was recrystallized from MeOH/Et$_2$O: mp 179°–181° C. Anal. calcd. for (C$_{18}$H$_{29}$N$_2$O$_2$Cl).

EXAMPLE 9

3-(2-aminoethyl)-5-(4-butyloxybutyloxy)-indole hydrochloride

A mixture of N-t-BOC-serotonin (276 mg, 1 mmol), 1-bromo-4-butyloxybutane (310 mg, 1.5 mmol) and K$_2$CO$_3$ (207 mg, 1.5 mmol) in acetonitrile (20 mL) was refluxed for 24 h under N$_2$ with stirring. After cooling to room temperature the solid was removed by filtration and solvent evaporated under reduced pressure to give an oil. The oil was purified by column chromatography (25% EtOCAc/hexane) to give 3-(N-t-BOC-2-aminoethyl)-5-(4-butyloxybutyloxy) indole as an oil.

To a solution of 3-(N-t-BOC-2-aminoethyl)-5-(4-butyloxybutyloxy) indole (403 mg, 1 mmol) in EtOAc (5 mL) was added 3N HCl in EtOAc (15 mL). The mixture was stirred for 2 h. The precipitated product was filtered and washed with EtOAc and Et$_2$O to give (80%) 3-(2-aminoethyl)-5-(4-butyloxybutyloxy) indole hydrochloride. Analytical sample was recrystallized from MeOH/Et$_2$O: mp 174°–176° C. Anal. calcd. for (C$_{18}$H$_{30}$N$_2$O$_2$Cl·0.25H$_2$O).

EXAMPLE 10

Also as described in example 2, but with appropriate selection of alkanoylhalide, there is produced the following ester compounds:

(i) 3-(2-aminoethyl)-5-heptanoyloxyindole, from heptanoylchloride;
(ii) 3-(2-aminoethyl)-5-octanoyloxyindole, from octanoylchloride;
(iii) 3-(2-aminoethyl)-5-nonanoyloxyindole, from nonanoylchloride;
(iv) 3-(2-aminoethyl)-5-decanoyloxyindole, from decanoylchloride;

EXAMPLE 11

Comparison of Binding Affinities and Selectivities

The compounds of Examples 2–10 were evaluated using cell types receptive specifically to 5-HT1Dβ ligands and to 5-HT1A ligands. The assay protocol generally entailed the incubation of membranes prepared from cells expressing the 5-HT1A receptor and cells expressing the 5-HT1Dβ receptor, with $^3$H-8-OH-DpAT or $^3$H-5HT, respectively. Increasing levels of the test compound were incubated with the radioligand and the membrane homogenates prepared from the recombinant cells. After a 15 minute incubation at 37° C., the incubation was terminated by vacuum filtration. The filters were washed with buffer and the filters were counted for radioactivity using liquid scintillation spectrometry. The affinity of the test compound for 5-HT1A or 5HT1Dβ receptor was determined by computer-assisted analysis of the data and determining the amount of the compound necessary to inhibit 50% of the binding of the radioligand to the receptor. Concentrations ranging from $10^{-11}$M to $10^{-5}$M of the test compound (Example 2) were evaluated. For comparison, sumatriptan, and other compounds structurally related to the test compound were also evaluated. The results are presented in Table 1 below, with reference to the Formula I structure in which R$^2$, R$^3$ and R$^4$ are each H:

TABLE 1

| R$^1$ | Compound | 5-HT1Dβ (Ki,nM) | 5-HT1Dβ/ 5HT1A |
|---|---|---|---|
| H | serotonin | 4.0 | 1 |
| CH$_3$(CH$_2$)$_6$O— | Example 2 | 1.0 | 38 |
| CH$_3$(CH$_2$)$_7$O— | Example 3 | 3.8 | 13 |
| CH$_3$(CH$_2$)$_8$O— | Example 4 | 1.2 | 260 |
| HOCH$_2$(CH$_2$)$_7$O— | Example 5 | 0.3 | 119 |
| (CH$_3$)$_2$CH(CH$_2$)$_6$O— | Example 6 | 14 | 85 |
| (CH$_3$)$_3$C(CH$_2$)$_6$O— | Example 7 | 2.3 | 400 |
| CH$_3$CH$_2$O(CH$_2$)$_6$O— | Example 8 | 0.4 | 180 |
| CH$_3$(CH$_2$)$_3$O(CH$_2$)$_4$O— | Example 9 | 2.5 | 30 |
| CH$_3$(CH$_2$)$_{10}$O— | reference | 21 | 42 |
| — | sumatriptan | 5.5 | 60 |

As the tabulated results reveal, either one or both of binding affinity and selectivity for the 5-HT1Dβ receptor are enhanced through extension of the 5-position chain.

To determine the agonist activity of the nonyl compound of Example 4 at the 5-HT1Dβ receptor, the compound was applied in varying concentrations ($10^{-12}$ to $10^{-6}$M) to 24-well plates containing cultures of 5-HT1Dβ-presenting CHO cells exposed to forskolin, a drug that non-specifically stimulates the enzyme adenylate cyclase. The potency of the compound in inhibiting forskolin-stimulated adenylate cyclase activity was determined by measuring the decrease in cAMP in the wells after 10 minute exposure to various concentrations of the compound. cAMP levels were determined using a radioimmunoassay kit containing antibody specific for cAMP and radioiodinated cAMP. The amount of the compound that inhibited 50% of the forskolin-stimulated adenylate cyclase activity was determined from the inhibition curve data subjected to computer assisted analysis (FIG. 1). The effect of $10^{-6}$ 5-HT was assayed in the same experiment for comparison purposes. The results of the assays indicate clearly that the nonyl compound is a potent, full agonist at the 5HT1Dβ receptor.

Using the functional assay just described, the activities of further compounds noted in the following table, were determined in a like manner:

| Concn (M) | Avg. cpm$^{125}$ | (S.E.M.) | % Inhib. cAMP |
|---|---|---|---|
| Example 5 $EC_{50}$ = 200 nM | | | |
| $10^{-9}$ | 4631 | 115 | 0 |
| $10^{-8}$ | 8130 | 2033 | 11 |
| $10^{-7}$ | 15118 | 767 | 33 |
| $10^{-6}$ | 33956 | 1339 | 92 |
| Example 7 $EC_{50}$ = 500 nM | | | |
| $10^{-8}$ | 5880 | 869 | 1 |
| $10^{-7}$ | 6137 | 279 | 3 |
| $10^{-6}$ | 16565 | 2022 | 79 |
| $10^{-5}$ | 19811 | 936 | 102 |

The reference compound identified in Table 1 ($R^1$= $CH_3(CH_2)_{10}O$—) was also evaluated in this functional assay and found to have a much inferior agonist activity ($EC_{50}$= 3500 nM). Such an activity result is predictable from the binding data presented in Table 1, and further supports the finding that, for optimum bioactivity, the 5'-substituent should have a chain length in the range from 8 to 11 atoms.

We claim:

1. A compound of the formula:

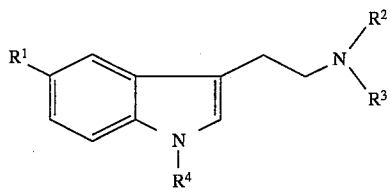

wherein $R^1$ represents a chain selected from $C_{8-11}$alkyl, $C_{7-10}$alkoxy, $C_{8-11}$alkanoyl and $C_{7-10}$alkanoyloxy wherein said chain is optionally substituted by hydroxyl, $C_{1-4}$alkyl or $C_{1-4}$alkoxy and wherein one of the intervening carbons of said chain is optionally replaced with a heteroatom selected from oxygen, nitrogen and sulfur;

$R^2$ and $R^3$ each independently represent H or $C_{1-3}$alkyl; and $R^4$ represents H, $C_{1-4}$alkyl, aryl or aryl$C_{1-4}$alkyl.

2. A compound according to claim 1, wherein $R^1$ is linear $C_{7-10}$alkoxy optionally substituted by hydroxyl, $C_{1-4}$alkyl or $C_{1-4}$alkoxy, wherein one of the intervening carbons of the chain is optionally replaced with an oxygen atom.

3. A compound according to claim 2, wherein $R^1$ is selected from nonyloxy; heptyloxy; octyloxy; 7,7-dimethyloctyloxy; 4-butyloxy-butyloxy; 6-ethyloxy-hexyloxy; and 8-hydroxy-octyloxy.

4. A compound according to claim 3, wherein $R^1$ is selected from 7,7-dimethyloctyloxy; 6-ethyloxy-hexyloxy; 8-hydroxyoctyloxy; and nonyloxy.

5. A compound according to claim 1, wherein $R^4$ is H.

6. A compound according to claim 5, wherein $R^1$ is linear $C_{7-10}$alkoxy optionally substituted by a group selected from hydroxyl, $C_{1-4}$alkyl and $C_{1-4}$alkoxy, wherein one of the intervening carbons of the chain is optionally replaced with an oxygen atom.

7. A compound according to claim 6, wherein $R^1$ is selected from nonyloxy; heptyloxy; octyloxy; 7,7-dimethyloctyloxy; 4-butyloxy-butyloxy; 6-ethyloxy-hexyloxy; and 8-hydroxy-octyloxy.

8. A compound according to claim 7, wherein $R^1$ is selected from 7,7-dimethyloctyloxy; 6-ethyloxy-hexyloxy; 8-hydroxyoctyloxy; and nonyloxy.

9. A compound according to claim 5, wherein $R^2$ is H.

10. A compound according to claim 9, wherein $R^1$ is linear $C_{7-10}$alkoxy optionally substituted by hydroxyl, $C_{1-4}$alkyl or $C_{1-4}$alkoxy wherein one of the intervening carbons of the chain is optionally replaced with an oxygen atom.

11. A compound according to claim 10, wherein $R^1$ is selected from nonyloxy; heptyloxy; octyloxy; 7,7-dimethylooctyloxy; 4-butyloxy-butyloxy; 6-ethyloxy-hexyloxy; and 8-hydroxy-octyloxy.

12. A compound according to claim 11, wherein $R^1$ is selected from 7,7-dimethyloctyloxy; 6-ethyloxy-hexyloxy; 8-hydroxyoctyloxy; and nonyloxy.

13. A compound according to claim 9, wherein $R^3$ is H.

14. A compound according to claim 13, wherein $R^1$ is linear $C_{7-10}$alkoxy optionally substituted by hydroxyl, $C_{1-4}$alkyl or $C_{1-4}$alkoxy wherein one of the intervening carbons of the chain is optionally replaced with an oxygen atom.

15. A compound according to claim 14, wherein $R^1$ is selected from nonyloxy; heptyloxy; octyloxy; 7,7-dimethyloctyloxy; 4-butyloxy-butyloxy; 6-ethyloxy-hexyloxy; and 8-hydroxy-octyloxy.

16. A compound according to claim 15, wherein $R^1$ is selected from 7,7-dimethyloctyloxy; 6-ethyloxyhexyloxy; 8-hydroxyoctyloxy; and nonyloxy.

17. A compound according to claim 16, wherein $R^1$ is nonyloxy.

18. A compound according to claim 16, wherein $R^1$ is 7,7-dimethyl-octyloxy.

19. A compound according to claim 16, wherein $R^1$ 8-hydroxy-octyloxy.

20. A compound according to claim 16, wherein $R^1$ 6-ethyloxy-hexyloxy.

21. A compound according to claim 1, wherein $R^2$, $R^3$ and $R^4$ are H and $R^1$ is selected from nonyloxy; heptyloxy; octyloxy; 7-methyl-octyloxy; 7,7-dimethyl-octyloxy; 4-butyloxy-butyloxy; 6-ethyloxy-hexyloxy; and 8-hydroxyoctyloxy and wherein said compound incorporates a radioactive atom.

22. A pharmaceutical composition, comprising a pharmaceutically acceptable carrier and a compound as defined in claim 1.

* * * * *